(12) United States Patent
Buhles et al.

(10) Patent No.: US 10,603,272 B2
(45) Date of Patent: Mar. 31, 2020

(54) STIMULATION OF APPETITE AND TREATMENT OF ANOREXIA IN DOGS AND CATS

(71) Applicant: Kindred Biosciences, Inc., Burlingame, CA (US)

(72) Inventors: William Buhles, Davis, CA (US); Richard Cortez, San Francisco, CA (US); Kristin Maas, San Francisco, CA (US); Geeta Srivastava, San Diego, CA (US); Daniel Perez, San Francisco, CA (US)

(73) Assignee: Kindred Biosciences, Inc., Burlingame, CA (US)

( * ) Notice: Subject to any disclaimer, the term of this patent is extended or adjusted under 35 U.S.C. 154(b) by 200 days.

(21) Appl. No.: 15/551,847

(22) PCT Filed: Feb. 26, 2016

(86) PCT No.: PCT/US2016/019730
§ 371 (c)(1),
(2) Date: Dec. 18, 2017

(87) PCT Pub. No.: WO2016/138357
PCT Pub. Date: Sep. 1, 2016

(65) Prior Publication Data
US 2018/0021251 A1  Jan. 25, 2018

Related U.S. Application Data

(60) Provisional application No. 62/126,188, filed on Feb. 27, 2015.

(51) Int. Cl.
*A61K 31/55* (2006.01)
*A61K 9/06* (2006.01)
*A61K 31/395* (2006.01)
*A61K 9/00* (2006.01)

(52) U.S. Cl.
CPC .......... *A61K 9/0014* (2013.01); *A61K 9/0017* (2013.01); *A61K 9/06* (2013.01); *A61K 31/395* (2013.01); *A61K 31/55* (2013.01); *A61K 9/0053* (2013.01)

(58) Field of Classification Search
CPC ...... A61K 9/0014; A61K 9/0017; A61K 9/06; A61K 31/395; A61K 31/55; A61K 9/0053
USPC .................................................... 514/213.01
See application file for complete search history.

(56) References Cited

U.S. PATENT DOCUMENTS

| 6,552,014 B2 | 4/2003 | Serebruany et al. |
| 6,589,556 B2 | 7/2003 | Cherukuri |
| 6,774,230 B2 | 8/2004 | Metzger et al. |
| 6,852,855 B2 | 2/2005 | Dolitzky |
| 6,946,141 B2 | 9/2005 | Tam et al. |
| 7,030,108 B2 | 4/2006 | Richter et al. |
| 7,041,826 B2 | 5/2006 | Handa et al. |
| 7,090,830 B2 | 8/2006 | Hale et al. |
| 7,541,371 B2 | 6/2009 | Arakawa et al. |
| 7,678,387 B2 | 3/2010 | Cherukuri |
| 7,994,314 B2 | 8/2011 | Kemperman et al. |
| 8,058,436 B2 | 11/2011 | Wieringa et al. |
| 8,173,804 B2 | 5/2012 | Maeda et al. |
| 8,574,626 B2 | 11/2013 | Vergez et al. |
| 8,754,119 B2 | 6/2014 | Scheller et al. |
| 9,078,810 B2 | 7/2015 | Setiawan et al. |
| 2001/0008896 A1 | 7/2001 | Smith et al. |
| 2002/0072602 A1 | 6/2002 | Singer |
| 2003/0096805 A1 | 5/2003 | Wang et al. |
| 2004/0176591 A1 | 9/2004 | Singer et al. |
| 2005/0074487 A1 | 4/2005 | Hsu et al. |
| 2006/0035889 A1 | 2/2006 | Tedford et al. |
| 2006/0127479 A1 | 6/2006 | Kumaraperumal et al. |
| 2007/0041905 A1 | 2/2007 | Hoffman et al. |
| 2007/0270413 A1 | 11/2007 | Houghton et al. |
| 2007/0298107 A1 | 12/2007 | Aluri et al. |
| 2008/0003275 A1 | 1/2008 | Vaisman |
| 2008/0014252 A1 | 1/2008 | DelPrete |
| 2008/0032937 A1 | 2/2008 | Yu et al. |
| 2008/0200533 A1 | 8/2008 | Krishnan |
| 2008/0255348 A1 | 10/2008 | Kemperman |
| 2008/0268021 A1 | 10/2008 | Warren et al. |
| 2008/0287774 A1 | 11/2008 | Katz-Brull |
| 2009/0186099 A1 | 7/2009 | Dugger, III |
| 2009/0203670 A1 | 8/2009 | Hoffmann et al. |
| 2009/0275749 A1 | 11/2009 | Maeda et al. |
| 2010/0129425 A1 | 5/2010 | De Graaff et al. |
| 2010/0179129 A1 | 7/2010 | Krishnan et al. |
| 2011/0046115 A1 | 2/2011 | Ahmed et al. |
| 2011/0053913 A1 | 3/2011 | Jhamandas et al. |

(Continued)

FOREIGN PATENT DOCUMENTS

| EP | 0431663 | 1/1994 |
| EP | 0813873 | 2/2002 |

(Continued)

OTHER PUBLICATIONS

Anonymous, "Mirtazapine Twist-a-Dose Transdermal Gel: Wedgewood Pet Rx," Apr. 30, 2014, retrieved from, 2 pages.
Arko et al., "Effects of Mirtazapine on the Levels of Exogenous Histamine in the Plasma of the Cat," Eur J Physiol, 2001, 442:R207-R208.
Avenatti et al., "Safety of Mirtazapine 2% Transdermal Ointment Administered Topically to Cats at 5 mg/kg for 28 Days [P10]," J Vet Intern Med, 2017, 31:1333-1334.

(Continued)

*Primary Examiner* — Yevgeny Valenrod
(74) *Attorney, Agent, or Firm* — McNeill Baur PLLC

(57) ABSTRACT

Pharmaceutical formulations and methods useful for the treatment of anorexia and the stimulation of appetite and weight gain, and the management of weight loss in dogs and cats.

32 Claims, 6 Drawing Sheets

(56) References Cited

U.S. PATENT DOCUMENTS

| | | | |
|---|---|---|---|
| 2011/0201804 A1 | 8/2011 | Bhanu et al. | |
| 2012/0095217 A1 | 4/2012 | Ritter et al. | |
| 2012/0149689 A1 | 6/2012 | Baker et al. | |
| 2012/0156144 A1 | 6/2012 | Tamarkin et al. | |
| 2013/0017262 A1 | 1/2013 | Mullen et al. | |
| 2013/0022676 A1 | 1/2013 | Mullen et al. | |
| 2013/0022677 A1 | 1/2013 | Mullen et al. | |
| 2013/0116242 A1 | 5/2013 | Baker | |
| 2013/0224284 A1 | 8/2013 | Mannino et al. | |
| 2013/0225559 A1 | 8/2013 | Peeters et al. | |
| 2013/0274247 A1 | 10/2013 | Quimby et al. | |
| 2013/0317122 A1 | 11/2013 | Setiawan et al. | |
| 2014/0154328 A1 | 6/2014 | Brkicic | |
| 2014/0271727 A1 | 9/2014 | Hwang et al. | |
| 2014/0271923 A1 | 9/2014 | Reid | |
| 2014/0323399 A1 | 10/2014 | Cowley et al. | |
| 2015/0098994 A1 | 4/2015 | Rariy et al. | |
| 2015/0148758 A1* | 5/2015 | Yoshitake | A61K 31/55 604/307 |
| 2015/0183786 A1 | 7/2015 | Wang et al. | |

FOREIGN PATENT DOCUMENTS

| | | |
|---|---|---|
| EP | 1067934 | 11/2003 |
| EP | 1223914 | 9/2004 |
| EP | 1209159 | 11/2004 |
| EP | 1030667 | 3/2005 |
| EP | 1066036 | 4/2006 |
| EP | 1273301 | 9/2006 |
| EP | 1829539 | 9/2007 |
| EP | 1442133 | 12/2007 |
| EP | 1941878 | 7/2008 |
| EP | 1768980 | 11/2008 |
| EP | 1729777 | 3/2009 |
| EP | 2133350 | 12/2009 |
| EP | 1225174 | 6/2010 |
| EP | 1238977 | 7/2010 |
| EP | 2247284 | 11/2010 |
| EP | 2283840 | 2/2011 |
| EP | 1439858 | 7/2012 |
| EP | 2377522 | 1/2013 |
| EP | 1879027 | 6/2013 |
| EP | 1773300 | 9/2013 |
| EP | 2632443 | 9/2014 |
| EP | 2012792 | 4/2015 |
| EP | 2146993 | 8/2015 |
| EP | 2650019 | 8/2015 |
| WO | WO 1999/059598 | 11/1999 |
| WO | WO 2000/076500 | 12/2000 |
| WO | WO 2003/075851 | 9/2003 |
| WO | WO 2003/086345 | 10/2003 |
| WO | WO 2004/010977 | 2/2004 |
| WO | WO 2004/084905 | 10/2004 |
| WO | WO 2004/100857 | 11/2004 |
| WO | WO 2005/016321 | 2/2005 |
| WO | WO 2005/034921 | 4/2005 |
| WO | WO 2005/063213 | 7/2005 |
| WO | WO 2005/089511 | 9/2005 |
| WO | WO 2006/088305 | 8/2006 |
| WO | WO 2007/012154 | 2/2007 |
| WO | WO 2007/019880 | 2/2007 |
| WO | WO 2007/050697 | 5/2007 |
| WO | WO 2007/057508 | 5/2007 |
| WO | WO 2007/061529 | 5/2007 |
| WO | WO 2007/063042 | 6/2007 |
| WO | WO 2007/064311 | 6/2007 |
| WO | WO 2007/135123 | 11/2007 |
| WO | WO 2007/146331 | 12/2007 |
| WO | WO 2008/060397 | 5/2008 |
| WO | WO 2008/116165 | 6/2008 |
| WO | WO 2008/104996 | 9/2008 |
| WO | WO 2009/018088 | 2/2009 |
| WO | WO 2009/055001 | 4/2009 |
| WO | WO 2011/091050 | 7/2011 |
| WO | WO 2012/026963 | 3/2012 |
| WO | WO 2013/038200 | 3/2013 |
| WO | WO 2013/158130 | 10/2013 |
| WO | WO 2013/183407 | 12/2013 |
| WO | WO 2014/195872 | 12/2014 |
| WO | WO 2015/049368 | 4/2015 |
| WO | WO 2015/075464 | 5/2015 |
| WO | WO 2015/085004 | 6/2015 |
| WO | WO 2015/092738 | 6/2015 |

OTHER PUBLICATIONS

Benson et al., "Drug Exposure and Clinical Effect of Transdermal Mirtazapine in Healthy Young Cats: a Pilot Study," J Feline Med Surg, 2016, 19:998-1006.

Benson et al., "Pharmacodynamics of transdermal mirtazapine in healthy client-owned cats," Colorado State University, Scientific Proceedings, 16$^{th}$ Annual Research Day, Jan. 31, 2015, 4 pages.

Berling et al., "Mirtazapine Overdose is Unlikely to Cause Major Toxicity," Clin Toxicol, 2014, 52:20-24.

Biswas et al., "The Pharmacovigilance of Mirtazapine: Results of a Prescription Event Monitoring Study on 13,554 Patients in England," J Psychopharm, 2003, 17:121-6.

Bremner et al., "Safety of Mirtazapine in Overdose," J Clin Psychiatry, 1998, 59:233-5.

Chang et al., "Efficacy of Mirtazapine in Preventing Intrathecal Morphine-Induced Nausea and Vomiting after Orthopaedic Surgery," Anaesthesia, 2010, 65:1206-1211.

Chen et al., "Premedication with Mirtazapine Reduces Preoperative Anxiety and Postoperative Nausea and Vomiting," Anesth Analg, 2008, 106:109-113.

De Boer, "The Pharmacologic Profile of Mirtazapine," J Clin Psychiatry, 1996, 57(Suppl. 4):19-25.

Extended European Search Report received in European Patent Application No. 16756426.9, dated Jul. 11, 2018, 11 pages.

Ferguson et al., Mirtazapine Toxicity in Cats: Retrospective Study of 104 Cases (2006-2011), Abstr. Amer College of Vet Int Med, Nashville, Jun. 4-7, 2014.

Ferguson et al., "Mirtazapine Toxicity in Cats: Retrospective Study of 84 Cases (2006-2011)," J Feline Med Surg, 2015, 18:868-874.

Fox et al., "Megestrol Acetate and Mirtazapine for the Treatment of Unplanned Weight Loss in the Elderly," Pharmacotherapy, 2009, 29:383-397.

Giorgi et al., "Pharmacokinetics of Mirtazapine and its Main Metabolites in Beagle Dogs: A Pilot Study," Vet J, 2011, 192:239-241.

Hernandez et al., "Severe Serotonin Syndrome Induced by Mirtazapine Monotherapy," Ann Pharmacotherapy, 2002, 36:641-3.

Himmerich et al., "Changes in Weight and Glucose Tolerance During Treatment with Mirtazapine," Diabetes Care, 2006, 29:170.

Kast, "Mirtazapine May be Useful in Treating Nausea and Insomnia of Cancer Chemotherapy," Support Care Center, 2001, 9:469-470.

Kast et al., "Cancer Chemotherapy and Cachexia: Mirtazapine and Olanzapine are 5-HT3 Antagonists with Good Antinausea Effects," Eur J Cancer Care, 2007, 16:351-354.

Kim et al., "Effectiveness of Mirtazapine for Nausea and Insomnia in Cancer Patients with Depression," Psychiatry Clin Neurosci, 2008, 62:75-83.

Kindred Biosciences, Inc., "FDA Approves Mirataz, a New Animal Drug to Manage Undesired Weight Loss in Cats," Press Release, May 14, 2018, 2 pages.

Kraus et al., "Body Weight, the Tumor Necrosis Factor System, and Leptin Production during Treatment with Mirtazapine or Venlafaxine," Pharmacopsychiatry, 2002,35:220-225.

Laimer et al., "Effect of Mirtazapine Treatment on Body Composition and Metabolism," J Clin Psychiatry, 2006, 67:421-424.

Longpre, et al., "Double-Blind, Placebo-Controlled, Randomized Study of Transdermal Mirtazapine Ointment for the Management of Feline Weight Loss [P11]," J Vet Intern Med, 2017, 31:1334.

Mason, et al., "Single Dose Pharmacokinetics Following Transdermal and Oral Administration of Mirtazapine 2% Transdermal Ointment in Cats [P12]," J Vet Intern Med, 2017, 31: 1334.

Montgomery, "Safety of Mirtazapine: A Review," Int Clin Psychopharmacol, 1995, 10(Suppl 4):37-45.

(56) References Cited

OTHER PUBLICATIONS

O'Banion et al., "Multiple Dose Pharmacokinetics of Mirtazapine 2% Transdermal Ointment in Cats," J Vet Intern Med, 2017, 31:1335.

Pae, "Low-Dose Mirtazapine may be Successful Treatment Option for Severe Nausea and Vomiting," Prog Neuropsychopharmacol Biol Psychiatry, 2006, 30:1143-1145.

Pfizer Product Monograph (Mirtazapine Orally Disintegrating Tablets 15 mg, 30 mg, and 45 mg), Mar. 29, 2012, accessed at http://www.pfizer.ca/en/our_products/products/monograph/320 on Jun. 22, 2014.

Quimby et al., "Studies on the Pharmacokinetics and Pharmacodynamics of Mirtazapine in Healthy Young Cats," J Vet Pharamcol Ther, 2011, 34:388-396.

Quimby et al., "The Pharmacokinetics of Mirtazapine in Cats with Chronic Kidney Disease and in Age-Matched Control Cats," J Vet Intern Med, 2011, 25:985-989.

Quimby et al., "Mirtazapine as an Appetite Stimulant and Anti-Emetic in Cats with Chronic Kidney Disease: A Masked Placebo-Controlled Crossover Clinical Trial," Vet J, 2013, 197:651-655.

Quimby et al., "Chronic use of Maropitant for the Management of Vomiting and Inappetence in Cats with Chronic Kidney Disease: A Blinded, Placebo-Controlled Clinical Trial," J Feline Med Surg, 2015, 17(8):692-697.

Quimby et al., "Assessment of Transdermal (Lipoderm) Mirtazapine as an Appetite Stimulant in Cats with Chronic Kidney Disease," J Vet Intern Med, 2017, 31:1594.

Riechelmann et al., "Phase II Trial of Mirtazapine for Cancer-Related Cachexia and Anorexia," Am J Hosp Palliat Care, 2010, 27:106-110.

Segers et al., "Can Mirtazapine Counteract the Weight Loss Associated with Alzheimer Disease? A Retrospective Open-Label Study," Alzheimer Dis Assoc Disord, 2014, 28:291-293.

Stahl, "Neuropharmacology of Obesity: My Receptors Made Me Eat It," J Clin Psychiatry, 1998, 59:447-448.

Stahl et al., "Which Comes First: Atypical Antipsychotic Treatment or Cardiometabolic Risk?" Acta Psychiatr Scand, 2009, 119:171-179.

Tack et al., "Efficacy of Mirtazapine in Patients with Functional Dyspepsia and Weight Loss," Clin Gastroenterol Hepatol, 2016, 14:385-392.

Timmer et al., "Mirtazapine Pharmacokinetics with Two Dosage Regiments and Two Pharmaceutical Formulations," Pharmaceut Res, 1997, 14:98-102.

Timmer et al., "Clinical Pharmacokinetics of Mirtazapine," Clin Pharmacokinetics, 2000, 38:461-474.

Waring et al., "Lack of Significant Toxicity After Mirtazapine Overdose: A Five-Year Review of Cases Admitted to a Regional Toxicology Unit," Clin Toxicol, 2007, 45:45-50.

Yin et al, "Prokinetic Effects of Mirtazapine on Gastrointestinal Transit," Am J Physiol Gastrointest Liver Physiol, 2014, 306:G796-801.

International Search Report for PCT/US2016/019730, dated May 2, 2016, 12 pages.

* cited by examiner

STIMULATION OF APPETITE AND TREATMENT OF ANOREXIA IN DOGS AND CATS

This application claims the benefit of priority to U.S. Provisional Application No. 62/126,188, filed Feb. 27, 2015, which is incorporated by reference herein in its entirety for any purpose.

FIELD

The present disclosure provides methods and pharmaceutical formulations for stimulating appetite and weight gain, managing weight loss, and treating anorexia in animals. The disclosure relates to the fields of biology, chemistry, pharmacology, and veterinary medicine.

DESCRIPTION OF RELATED DISCLOSURES

Anorexia is a common occurrence in animals. Both dogs and cats manifest anorexia when suffering from acute and chronic illness. Old age typically results in body weight loss for unknown reasons. Likewise dental dysfunction may lead to an unwillingness to eat. Chronic renal dysfunction and failure is characterized by weight loss, especially in cats. Further, in cats a sudden cessation of eating can predispose the animal to a serious or fatal liver failure. Adequate nutrition in cats is so important that anorexia is often treated by placement of a nasogastric tube, or surgical insertion of a feeding tube directly into the esophagus. Pharmacologic means to stimulate appetite, facilitate weight gain and manage weight loss are needed for dogs and cats.

Several drugs are used in animals specifically for the stimulation of appetite (orexigenic effect) (Plumb, *Veterinary Drug Handbook*, 7$^{th}$ Edition, Wiley-Blackwell, Ames Iowa). Among them are diazepam, cyproheptadine, and maropitant. The most commonly used is mirtazapine, an antidepressant approved for marketing in many countries for the treatment of depression in humans. Mirtazapine is administered orally in man. Studies of mirtazapine pharmacokinetics and appetite stimulation in cats show that oral administration stimulates appetite (Quimby et al. *J. Vet. Pharm. Therap*, 2010, 34:388-396. Quimby et al. *J. Vet. Intern. Med.* 2011; 25:985-989.). The typical oral dose of mirtazapine in cats is 1 to 5 mg per cat per day or every other day.

In cats, mirtazapine is rapidly absorbed following oral administration, appearing in the plasma within 1 hour and reaching a peak plasma concentration of approximately 126 to 250 ng/mL at 1 hour after an oral dose of 1.88 to 3.75 mg (Quimby et al *Vet Pharmacology Therapeutics*, 2010; 34:388-396). Moreover, at this dose the plasma half-life is 9.2 to 15.9 hours. In dogs, 20 mg mirtazapine given orally results in a peak plasma concentration of 164 ng/mL at 1 hour with a plasma half-life of 6.2 hours (Giorgi et al. *Vet Journal*, 2012; 192:239-241).

Also used for the stimulation of appetite in dogs and cats are the chemicals diazepam, cyproheptadine, and maropitant. However, diazepam is a potent sedative agent and this side effect can limit the dose given. In addition, diazepam must be given intravenously and can be associated with a severe hepatic lipidosis in cats. Cyproheptadine can also result in sedation in cats, or sometimes can result in serious paradoxical agitation and mania. None of these compounds has gained widespread use as an orexigenic medication.

One of the disadvantages of treating cats and dogs with mirtazapine is that the drug is given orally. See, for example, PCT Patent Publication WO2013158130, incorporated herein by reference, where tablets containing 1.88 mg mirtazapine were administered orally to stimulate appetite in cats with renal dysfunction. Oral administration of drugs to these animals, however, can be difficult. Cats often resist oral administration and can injure themselves or their handlers. In addition, cats are very sensitive to the taste of medications and can react strongly to pharmacologic agents administered orally, often with hypersalivation and emesis. Dogs likewise can be difficult to dose orally. The problem is amplified by the fact that these animals already are not eating normally, and so orally dosing them can be even more difficult than usual.

Some pharmacies compound a mirtazapine ointment (see, e.g., Wedgewood Pharmacy) that is applied to the skin of a cat in an attempt to achieve transdermal absorption of therapeutically effective amounts of mirtazapine into the systemic circulation. However, absorption of such compounded preparations is highly variable and can result in undesired drug levels, including both peak plasma concentration levels that are too high, and drug not remaining in the circulation at therapeutically effective levels for the desired time period.

There is the need for pharmaceutical formulations of mirtazapine which makes administration to cats and dogs consistent, safe, efficacious, and practical.

The present disclosure provides methods and pharmaceutical formulations of the orexigenic compound mirtazapine for stimulation of appetite in cats and dogs. Use of these methods and formulations provides appetite stimulation, weight gain, and concomitant management of weight loss, that is superior to presently used methods by providing accurate dosing, more efficient delivery of drug, improved pharmacokinetics and pharmacodynamics, safer drug delivery, and more controlled drug effects, and hence greater efficacy than currently used methods and treatments. Importantly, the methods and formulations described herein provide for more convenient application of a topical formulation of mirtazapine that can be transdermally absorbed and maintained at therapeutically effective levels sufficient to treat anorexia and otherwise stimulate appetite in dogs and cats and manage weight loss in these animals.

SUMMARY

In a first aspect, the present disclosure provides methods for the treatment of anorexia and for appetite stimulation, causing weight gain, and/or management of weight loss, comprising the administration of mirtazapine to a dog or a cat. In a preferred embodiment, the administration is topical.

In a second aspect, the present disclosure provides for pharmaceutical formulations for topical administration of mirtazapine to dogs or cats. These formulations include, but are not limited to, ointments, creams, and pastes. In a preferred embodiment, the formulation is a topically applied ointment that maintains mirtazapine in solution in the formulation such that a therapeutically effective dose can be topically administered. In various embodiments, the methods provided herein are practiced such that the topically administered ointment is applied at a location on the cat or dog that deters inadvertent oral administration of the formulation, i.e., the ointment is administered on or around the ear or neck of a cat or dog where the animal would be less likely to ingest it. In preferred embodiments, the ointment comprises at least 0.2% to about 4% by weight (w/w), mirtazapine (for purposes of the w/w percentages provided herein, assume the HCl salt is employed in the formulation, although any pharmaceutically acceptable form may be used), e.g., 2% to 4% w/w mirtazapine, and at least 25%, by weight, of mixtures of penetration enhancers and solubilizers. In some preferred embodiments, the formulation is a formulation exemplified in the examples below.

In various preferred embodiments, the formulation is applied as an ointment in an amount ranging from 0.05 mL to 0.2 mL for the cat, and 0.05 mL to 2 mL for the dog (given their larger size range) from a device such as, but not limited to, a (needle-less) syringe or pen or tube (with blunt tip suitable for ointment application) containing from one to up to about 5 or more mL (but typically 60 mL or less) of a mirtazapine ointment formulation provided herein. In some embodiments, a 2% w/w mirtazapine formulation is applied in a therapeutically effective dose of about 0.1 mL to the skin of an animal, e.g., a cat. In certain embodiments, the mirtazapine formulation is applied in a therapeutically effective dose to the ear of an animal, e.g., a cat. In certain such embodiments, the mirtazapine formulation is applied in a therapeutically effective dose to the anterior surface of the ear flap (the pinna) of the animal, e.g., a cat.

Exemplary formulations provided herein include those containing 0.2 to 4% w/w mirtazapine (2 to 40 mg/mL), e.g., 2% w/w mirtazapine or 4% w/w mirtazapine, which may provide a mirtazapine dose in the range of about 0.05 mg/kg to 5.0 mg/kg, or about 0.05 mg/kg to 3.0 mg/kg, or about 0.5 mg/kg to 3.0 mg/kg, or about 1 mg/kg, or about 2 mg/kg, and peak blood plasma levels in the range of 10 ng/mL to 30 ng/mL (as measured in single dose studies). In some embodiments, the formulations provided herein provide a peak blood plasma level of mirtazapine in a range of 10 ng/ml to 150 ng/ml, or 10 ng/ml to 120 ng/ml, or 10 ng/ml to 100 ng/ml, or 10 ng/ml to 60 ng/ml, or 10 ng/ml to 30 ng/ml. In some embodiments, such formulations provide a typical in vivo mirtazapine half-life can be about 20-32 hours, such that each therapeutically effective administration achieves an AUC in the range of 250-1000 h*ng/mL, including but not limited to an AUC in the range of 450-650 h*ng/mL (as measured in single dose studies). In some embodiments, the formulations provided herein provide an AUC in the range of 300 to 1200 h*ng/ml in the 24 hour period immediately following application of the formulation, or in the range of 300 to 1000 h*ng/ml in the 24 hour period immediately following application of the formulation. In various embodiments, administration of a formulation provided herein maintains blood levels of mirtazapine in the 10 to 30 ng/mL range in the treated animal for at least 12 hours (as measured in single dose studies), or at least 10 ng/ml for at least 6 hours during the 24 hour period immediately following administration of the formulation, or in a range of 10 ng/ml to 30 ng/ml for at least 6 to 12 hours during the 24 hour period immediately following administration of the formulation.

The ointments described herein are composed in part of chemicals that enhance transdermal absorption of mirtazapine through the skin. Preferred formulations include up to at least about 25%, by weight (w/w), of a penetration enhancer or solubilizer. In some embodiments, the percentage is at least about 30%. In some embodiments, the percentage is about 30.5%. Ointment formulations and other mirtazapine formulations useful in the methods described herein may comprise one or more antioxidant agents to improve stability of the mirtazapine. The present disclosure also provides for various containers containing the ointments or other mirtazapine formulations useful in the methods described herein. Such containers include various tubes, syringes, bottles, and the like, and provide protection of the formulation from air, moisture, and/or light.

In a third aspect, the present disclosure provides methods of applying such topical ointment formulations having these special formulation characteristics to dogs or cats to achieve increased transdermal absorption. In other embodiments, methods provided herein may be practiced using other formulations, including other ointments, creams, gels, pastes, or solutions, such as those that provide delayed release of drug during transdermal absorption and/or otherwise utilize delayed-release transdermal drug formulation technology, i.e., so that dosing can be done less frequently (at more prolonged intervals between doses), or those methods may be practiced using devices such as patches that enhance transdermal absorption. In preferred embodiments, particularly advantageous using the novel ointments described herein, the formulation is topically applied once daily for one or more consecutive days, including for at least a week, 2 weeks, a month, a year, and even, in some instances, for the rest of the animal's life.

In a fourth aspect, the present disclosure provides for a device for the delivery of a semi-solid mirtazapine formulation, including the novel ointment formulations described herein, said device designed to deliver a small volume of drug product consistently and accurately. In a preferred embodiment, the device is in the form of a syringe or pen containing at least one and typically more than one, including, without limitation, five, seven, ten, fourteen, 20, 30, or more daily doses of mirtazapine. In various embodiments, the barrel of the syringe or pen can contain from 1 mL to 10 mL, or 1 mL to 50 mL, or even 1 mL to 100 mL, such as 60 mL, of a mirtazapine formulation provided herein. In some embodiments, the barrel contains 5 mL to 6 mL of a formulation provided herein, including but not limited to an ointment, such as ointment T, described in the examples below. In some embodiments, the barrel of the syringe or pen contains from 0.5-10 g of a mirtazapine formulation. In some embodiments, the barrel of the syringe or pen contains from 3-7 g of a mirtazapine formulation. In certain such embodiments, the barrel contains 5-6 g of a mirtazapine formulation, or approximately 5 g of such formulation.

In some embodiments, the device used to administer a formulation described herein is a cosmetic pen, as a non-limiting example, of the type marketed by Yiwu Tima Cosmetic Packaging Co., Ltd., under "twist up design or click pen cosmetic packaging". Other suitable device formats for administration of a formulation described herein include, without limitation, the applicator pens described in U.S. Pat. Nos. 8,292,529, and 8,540,124, each of which is incorporated herein by reference, as well as the applicator pen which may be used to administer the topical mirtazapine formulation that is marketed under "Twist-a-Dose" by Wedgewood Pharmacy.

DETAILED DESCRIPTION

Figure 1:
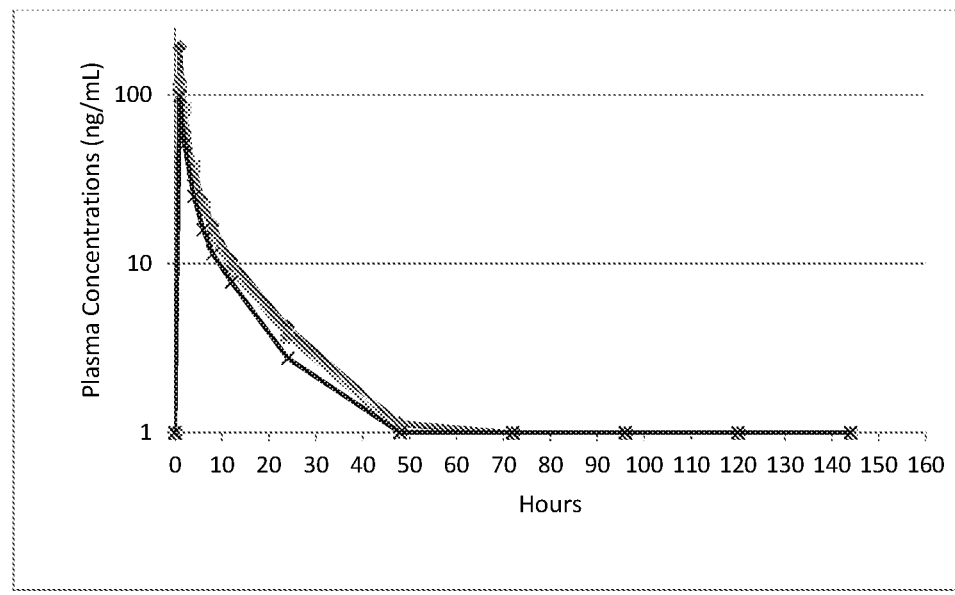
FIG. 1 is a graph showing plasma concentration of mirtazapine over time following a single oral administration of a commercially available oral tablet formulation of mirtazapine to each of four healthy cats. See Example 1.

In some embodiments, the present disclosure provides a pharmaceutical formulation of mirtazapine that is an ointment intended for topical administration. This aspect of the disclosure arose in part from overcoming substantial challenges for delivering mirtazapine to a cat or dog topically to facilitate ease of administration and enhance therapeutic efficiency. These challenges included the solubility constraints and base incompatibilities imposed by mirtazapine, which has to be in solution for effective transdermal absorption. This required an ointment for optimal delivery, as a cream is made up of at least two immiscible phases and to keep the mirtazapine in solution, a more soluble product is preferred. A solution or other liquid formulation would be at risk of shedding and running, depending on the site of application but clearly suboptimal for a furred animal such as most cats and dogs. The present disclosure provides novel ointment formulations of mirtazapine that have sufficiently high viscosity to remain in place after application topically and deliver therapeutically effective doses transdermally. To facilitate description of the invention and better appreciation of its advantages, the following definitions are provided.

Definitions

Unless defined otherwise below, all technical and scientific terms used herein have the same meaning as is commonly understood by one of ordinary skill in the art to which this disclosure pertains.

The terms "a" and "an" and "the" and similar referents as used herein refer to both the singular and the plural, unless otherwise indicated herein or clearly contradicted by context.

The term "about" as used herein refers to greater or lesser than the value or range of values stated by 1/10 of the stated values, but is not intended to limit any value or range of values to only this broader definition. For instance, a value of "about 30%" means a value of between 27% and 33%. Each value or range of values preceded by the term "about" is also intended to encompass the embodiment of the stated absolute value or range of values. Recitation of ranges of values herein are merely indented to serve as a shorthand method of referring individually to each separate value inclusively falling within the range, unless otherwise indicated herein, and each separate value is incorporated into the specification as if it were individually recited herein.

The phrase "bulking agent" refers to an excipient suitable for use in a pharmaceutical formulation that is inert and simply provides the product with more mass than it would have otherwise. Suitable bulking agents for use in the pharmaceutical formulations of the disclosure include, without limitation, polyethylene glycol (PEG), such as PEG 400 and PEG 3350.

The term "cream" refers to a type of emulsion, comprising at least two immiscible liquid phases, one dispersed in the form of drops or droplets within the other. Creams typically are intended for external application to the skin or mucous membranes.

The term "ointment" refers to a pharmaceutical formulation that is a semisolid preparation intended for external application to the skin or mucous membranes and are compositions derived from four "ointment bases," which are hydrocarbon bases, absorption bases, water-removable bases, and water-soluble bases. The Merck Veterinary Manual defines "ointment" as a greasy, semi-solid preparation that contains dissolved or dispersed drug. Ointment bases include hydrocarbons, vegetable oils, silicones, absorption bases consisting of a mixture of hydrocarbons and lanolin, emulsifying bases consisting of a mixture of hydrocarbons and an emulsifying agent, and water-soluble bases. Ointment bases influence topical drug bioavailability by (i) their occlusive properties that hydrate the stratum corneum, which can enhance drug flux across the skin; and (ii) their properties that affect drug dissolution within the ointment and drug partitioning from the ointment to the skin.

The term "paste" refers to a pharmaceutical formulation that is a semisolid preparation of stiff consistency intended for external application to the skin, oral cavity, or mucous membranes.

The phrase "penetration enhancer" refers to an excipient suitable for use in a pharmaceutical formulation described herein, such as, but not limited to, an ointment, that facilitates absorption of a drug into the skin. Suitable penetration enhancers for use in the pharmaceutical formulations described herein include, but are not limited to, Di-ethylene Glycol Monoethyl Ether (DGME) and PEG-8 Caprylic/Capric Glycerides (Labrasol®).

The phrase "pharmaceutical formulation" refers to a composition intended for therapeutic use that is safe and effective for its intended use. A formulation safe and effective for one type of use, such as topical application, may in some embodiments not be safe for another type of use, such as IV administration. Thus, as used herein, "pharmaceutical formulation for topical administration", for example, excludes any type of pharmaceutical formulation that would not be safe or effective for its intended use.

The term "preservative" refers to an excipient suitable for use in a pharmaceutical formulation described herein, such as, but not limited to, an ointment, that functions to maintain the drug in a desired physical state. A preservative may have anti-microbial or anti-oxidant properties or may otherwise serve to protect the drug, e.g., from exposure to light or air. Butylated hydroxytoluene (BHT) is a nonlimiting example of a suitable preservative in the ointment formulations described herein.

The term "solubilizer" refers to an excipient suitable for use in a pharmaceutical formulation described herein, such as an ointment, that facilitates dissolution of a drug into another substance. Suitable solubilizers for use in the pharmaceutical formulations described herein include, but are not limited to, DGME, Labrasol®, and oleyl alcohol.

The term "solution" refers to a homogenous liquid preparation that contains one or more chemical substances dissolved in one or a mixture of miscible solvents.

The phrase "spreading agent" refers to an excipient suitable for use in a pharmaceutical formulation described herein, such as an ointment, that facilitates the dispersion or absorption of one substance with or into another, i.e., a spreading agent may facilitate dissolution of one substance into another and/or the distribution of any component of a formulation amongst any other component(s) and/or application of an ointment to the skin. Suitable spreading agents for use in the pharmaceutical formulations described herein include, without limitation, silicon and silicon derivatives, such as Polydimethylsiloxane fluid (Q7-9120 Silicone Fluid 20 CST), Aluminum Starch Octenylsuccinate (Dry Flo®), and PEG are examples of spreading agents.

Certain compounds may have more than one of the above-defined properties. As one nonlimiting example, PEG has the properties of both a bulking agent and a spreading agent. In another nonlimiting example, DGME and Labrasol® can serve as both penetration enhancers and solubilizers. In certain embodiments, it may be advantageous to use a formulation component having more than one of the desired properties for the formulation to reduce overall cost and complexity of the formulation while retaining the desired formulation properties.

The phrase "therapeutically effective dose" refers to that amount of a drug (an "active pharmaceutical ingredient" or "API") that is administered simultaneously or contemporaneously in one administration (in some embodiments multiple unit dose forms, i.e., pills, tablets, capsules, or injections, can be administered in one administration) to achieve a desired therapeutic outcome, even if multiple administrations over time are administered in the course of therapy.

In some embodiments, the appetite stimulating compound mirtazapine is present in a pharmaceutical formulation to be given to a dog or a cat to stimulate appetite and cause weight gain, to treat anorexia, or to manage weight loss. Mirtazapine may be given by all medically acceptable routes of administration, including but not limited to topically, orally, intravenously, intraperitoneally, subcutaneously, intramuscularly, or rectally. In certain embodiments, the mirtazapine is topically applied, such as in the form of an ointment.

The therapeutically effective dose for practice of the methods provided herein is in the range of 0.05 mg to 5 mg mirtazapine/per kg weight of animal (mg/kg) per dose, or 0.05 to 3 mg/kg per dose, or 0.05 to 2 mg/kg per dose, or 0.5 to 3 mg/kg per dose, or 0.5 to 2 mg/kg per dose. Typically, the therapeutically effective dose is administered once daily, and daily administration continues for several days or longer, but single day treatments can be effective in some animals for some purposes. Generally, however, treatment will continue on consecutive days for several days to a week, several weeks, a month, several months, or even the rest of the animal's life. In cats (or dogs or any other animal) the dose may be adjusted according to the weight of the animal to be treated. Expressed in such terms, illustrative therapeutically effective doses include those in the dosage range of 0.05 to 2 mg/kg per daily dose administered once per day. Alternatively, a therapeutically effective dosage in accordance with the disclosure may be expressed as a dose per animal, such as 0.1 to 5.0 mg per dose per cat or 0.5 to 50 mg per dose per dog. The therapeutically effective dose is typically given once daily but may be given every other day or once weekly or at other frequencies dependent upon the formulation chosen and intended use. In some embodiments, the formulation used in the method is topically applied with the mirtazapine largely transdermally absorbed and provides peak blood plasma levels in the range of 10 to 30 ng/mL, and a half-life of at least 12 hours or longer, e.g., 15-24 hours. In another embodiment, topical administration with an ointment formulation described herein is continued for 2, 3, 5, 7, or more consecutive days, including for one, 2, 3, 4 or more weeks, including for one, 2, 3, 4, 5, or 6 or more months.

In some embodiments, the present disclosure provides a pharmaceutical formulation that is an ointment, cream, and paste or other suitable semi-solid form that can be applied to the pelt of a dog or cat to provide for oral ingestion of the formulation when the animal licks itself to clean the site of application. In preferred embodiments, however, the formulation is an ointment or other suitable semi-solid form that is applied to the animal's skin at a site where the animal is unable to lick or otherwise reach to consume the dose orally: in this embodiment of the methods provided herein, the drug is transdermally absorbed into the animal's bloodstream. In some embodiments, the formulation is applied to the pinna, such as the anterior pinna.

Thus, in some embodiments, the present disclosure provides a pharmaceutical formulation that is an ointment or other suitable semi-solid form that can be applied to the skin of a dog or cat to provide for transdermal absorption of mirtazapine through the skin and into the systemic circulation. Preferred formulations of the disclosure include at least about 25%, by weight, of a mixture of penetration enhancers/solubilizers, including without limitation the formulations described in the examples below. Suitable formulations generally include, in addition to 25-35% w/w penetration enhancer/solubilizer, 4-6% spreading agent; 50-70% bulking agent; 0.2 to 4% by weight active pharmaceutical ingredient (mirtazapine hemihydrate or equivalent amount of another salt, such as mirtazapine HCl); and an antioxidant (less than 1%, typically less than 0.1%).

The examples below show preferred ointment formulations. The specifically exemplified ointments in the examples and the more generic descriptions of them here result from the discoveries made in overcoming the solubility challenges proposed by including mirtazapine in an ointment at a concentration that could provide a therapeutically effective dose in a conveniently administered amount and form and selecting from known excipients particular combinations that provide especially beneficial results. Non-limiting exemplary excipients in the ointment formulations are penetration enhancers, solubilizers, bulking agents and spreading agents.

In some embodiments, the pharmaceutical formulation is an ointment or other solid or semi-solid form with extended release characteristics that allow for slower release and absorption than an immediate release formulation and provides for dosing at longer intervals, for example once daily or once weekly.

In other embodiments, however, the pharmaceutical formulation used in a method described herein is an immediate release formulation for topical use, such as Formulations G, H, and T, described in the examples below. These formulations are ointments that are applied so that the mirtazapine is transdermally absorbed into the circulatory system of the target animal, typically a cat or dog, where peak plasma levels are in the 10 ng/mL to 30 ng/mL range and the mirtazapine half-life is at least 12 and more typically about 22 hours or longer, as measured under test conditions using single doses similar to those employed in the examples below. In some embodiments, a formulation provided herein provides a peak blood plasma levels of mirtazapine in a range of 10 ng/ml to 150 ng/ml, or 10 ng/ml to 120 ng/ml, or 10 ng/ml to 100 ng/ml, or 10 ng/ml to 60 ng/ml, or 10 ng/ml to 30 ng/ml. In some embodiments, a formulation provided herein provides blood plasma levels of mirtazapine of at least 10 ng/ml for at least 6 hours during the 24 hour period immediately following application of the formulation to the pinna, or in a range of 10 ng/ml to 30 ng/ml for at least 6 to 12 hours during the 24 hour period immediately following application of the ointment to the skin. Such formulations allow for lower plasma and tissue concentrations of the chemical for a longer period of time than can be achieved with other formulations, such as an oral dosing formulation. Such formulations also have the advantages described herein of improved administrability to the animal.

Very high plasma concentrations (greater than about 50 ng/mL) are associated with adverse effects of mirtazapine in cats, including behavioral changes and hyperactivity; therefore, the transdermally absorbed ointment formulations described herein, which exhibit generally lower peak concentrations and maintain therapeutically effective levels in the target animal for longer times, relative to the oral formulations, represent a significant advance over them.

In some embodiments, the formulation may be of such a nature to dry on the skin. In some such embodiments, the formulation may be a quick drying formulation such that the topical mirtazapine cannot be licked or rubbed off of the surface of the skin shortly after application.

In some embodiments, the topically administered ointments and other topically applied formulations useful in the methods described herein provide transdermal absorption over a relatively prolonged period of time (such as at least 6 to 8 hours or longer, e.g., 12 hours or longer, including up to 22 hours or longer).

Alternatively, in some embodiments, the objective may be met by other topically applied formulations. For example, such formulations may contain microparticles of a variety of types to delay release of mirtazapine from the formulation and/or enhance its absorption through the skin and/or into the vascular system. The microparticles may be composed of organic polymers, polysaccharides, oil-in-water droplets, or other compounds and vehicles to effect slow diffusion of mirtazapine into the skin.

In various embodiments, the present disclosure provides a pharmaceutical formulation that is an ointment that contains a penetration enhancer, such as a surfactant or solvent or other agent which enhances transdermal absorption and which can be applied to the skin, and a non-aqueous solubilizer to assure that the mirtazapine is in solution in the preparation, mirtazapine being insoluble in water. In various embodiments, a preservative, including but not limited to an antioxidant compound, is incorporated into the ointment. In various formulations, an anti-oxidant is included to stabilize the mirtazapine from oxidation; BHT is a suitable antioxidant for this purpose, for example and without limitation. Other suitable antioxidants include, without limitation, BHA (Butyl Hydroxy Anisole).

In some embodiments, the pharmaceutical formulation for topical application, such as an ointment, cream, or paste, is provided in a container that is air-tight and moisture resistant to prevent the formulation coming into inadvertent contact with air or moisture. In some embodiments, the formulation is provided in a container that is amber or black or opaque to prevent light from affecting the stability of the mirtazapine. In some embodiments, some or all of the manufacturing steps used to make the pharmaceutical formulation are conducted in the absence of air (e.g., under nitrogen) to prevent degradation of the drug.

In various embodiments, the ointment composition has an odor that not unpleasant to cats, as even a mild irritant in this regard will quickly make the cat resist (sensitize the cat to) application of the ointment. In preferred embodiments for use with felines, the ointment is odorless. In various such embodiments, the formulation does not comprise ethanol. Similarly, preferred ointments for felines utilize excipients selected for being non-irritants, i.e, non-inflammatory, because the cat's pinna, the site of application to the feline in many embodiments, is highly vascularized with very thin skin. Inflammation in that area might not only sensitize the cat to application of the drug but even more seriously lead to undesirable alteration of the absorption properties, preventing administration of therapeutically effective levels, and potentially resulting in higher, undesired levels.

In some embodiments, the mirtazapine formulation comprises 20-80%, or 20-70%, or 30-80%, or 30-70%, or 40-80%, or 40-70%, or 50-80%, or 50-70% of polyethylene glycols. In some embodiments, the polyethylene glycols include one or more of polyethylene glycol 400, polyethylene glycol 3350, polyethylene glycol 4000, polyethylene glycol 2000, or polyethylene glycol 6000. In some embodiments, the polyethylene glycols include polyethylene glycol 400. In some embodiments, the polyethylene glycols include polyethylene glycol 3350. In some embodiments, the polyethylene glycols include polyethylene glycol 400 and polyethylene glycol 3350. In some embodiments, the mirtazapine formulation comprises 20-60% polyethylene glycol 400 and 10-50% polyethylene glycol 3350. In some embodiments, the mirtazapine formulation comprises 30-50% polyethylene glycol 400 and 10-30% polyethylene glycol 3350. In some embodiments, the mirtazapine formulation comprises 30-45% polyethylene glycol 400 and 20-25% polyethylene glycol 3350.

In some embodiments, the mirtazapine formulation comprises 15-25% diethylene glycol monoethyl ether (DGME). In some embodiments, the mirtazapine formulation comprises 5-10% PEG-8 caprylic/capric glycerides. In some embodiments, the mirtazapine formulation comprises 3-8% oleyl alcohol. In some embodiments, the mirtazapine formulation comprises 0.5-3% polydimethylsiloxane fluid. In some embodiments, the mirtazapine formulation comprises 1-4% Tapioca Starch Polymethylsilsequioxane (Dry Flo TS).

In some embodiments, the mirtazapine formulation does not comprise ethanol. In some embodiments, the mirtazapine formulation does not comprise hydroxypropylcellulose.

In some embodiments, the mirtazapine ointment, cream, or paste for topical application is contained in an applicator device to allow small increments (e.g., 0.1, 0.2, or 0.5 mL) of product to be dispensed as the device is activated by the user. The increments of product dispensed range from 0.05 to 0.3 mL, such as 0.1 mL, for use in cats and 0.1 to 2.0 mL, such as 0.5 mL, for use in dogs and the device allows for accurate and consistent dosing, which may be important to avoid untoward effects secondary to high plasma concentrations, at least for some animals. Such devices are known in the art for use with other drugs, particularly ointments for human or animal topical application but have not been previously used to deliver mirtazapine to animals in accordance with the methods described herein. In some embodiments, the "Twist-a-Dose" applicator of Wedgewood Pharmacy (http://www.wedgewoodpetrx.com/items/methimazole-prednisolone-twist-a-dose-transdermal-gel.html) may be used. In addition, such devices, or other devices intended to administer only a set quantity of ointment or other formulation, have the advantage of more accurate dosing and otherwise limiting undesired contact with the drug (i.e., as could result from too much drug being dispensed, for example, such that the veterinarian or other applicator, as well as the animal, have excessive contact), and generally make administration simpler to use.

In other embodiments, however, simpler devices are readily and easily employed in the methods provided herein. For example, the present disclosure provides containers composed of an aluminum tube with a tapered aluminum tip to control dosing. In some embodiments, this or a similar product is packaged in a carton box with product insert. In those and in other embodiments, the container is typically labeled with product information, including directions for use.

In various embodiments, treatment in accordance with this disclosure will increase appetite as measured by an increase in the consumption of food in a given time period, or by weight gain or management of weight loss of the animal. Methods of managing weight loss are provided, for example, for animals (such as cats and dogs) that are losing weight due to age, illness, and the like. Managing weight loss in such animals includes, for example, slowing the weight loss, stopping the weight loss (such that a constant weight is achiever), and reversing the weight loss. Such weight gain or management of weight loss will improve the quality of life and longevity of the animal.

EXAMPLES

Figure 2:
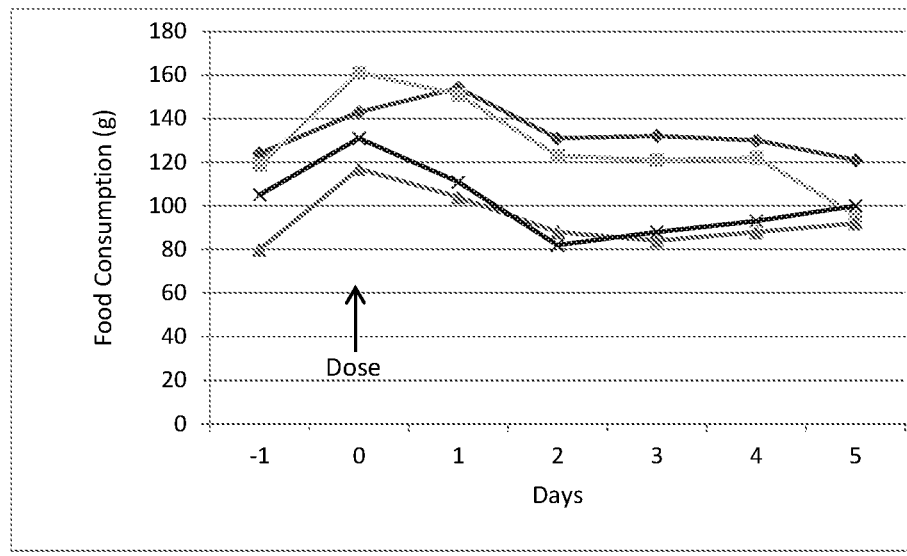
FIG. 2 is a graph showing grams of food consumed over time following a single oral administration of a commercially available oral tablet formulation of mirtazapine to each of four healthy cats, as described in Example 1.

Example 1. Demonstration of Therapeutic Efficacy of Oral Mirtazapine for the Stimulation of Appetite in Cats A measured portion of a 45 mg commercial tablet (Remeron®) of mirtazapine was prepared by cutting and weighing and administered orally to four adult cats at a dosage of 0.5 mg/kg. In this demonstration, venous blood samples were taken at measured intervals to quantify the amount of mirtazapine in the plasma. Food consumption and activity were measured. The cats remained active and demonstrated no adverse effects from the treatment. Plasma concentrations of mirtazapine following oral dosing are summarized in FIG. 1. Peak plasma concentrations of mirtazapine were in the range of 50 to 150 ng/mL (mean 131), the peak concentration occurred at 1 to 2 hours after dosing, the total drug exposure as measured as area under the curve ("AUC") was 250 to 750 (mean 507) h*ng/mL, and the half-life was 10 hours. Food consumption during the study was determined by weight of food consumed, and is shown in FIG. 2.

Example 2. Demonstration of Variable Therapeutic Efficacy of a Topical (Transdermal) Commercially Available Compounded Formulation of Mirtazapine for the Stimulation of Appetite in Cats A measured amount of a commercially available compounded mirtazapine ointment (Wedgewood Pharmacy) to deliver a dosage of 0.5 mg/kg was applied onto the skin of the inner (anterior) surface of the ear flap (pinna) of four cats, using the manufacturer's applicator and instructions (available in video form at www.youtube.com/watch?v=1R6CE5-WKQo).

Figure 3:
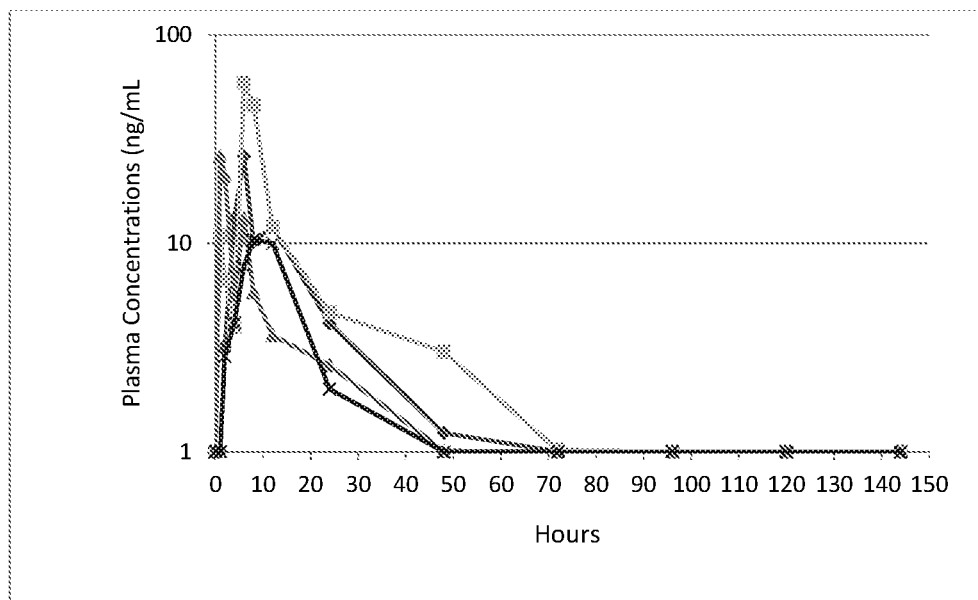
FIG. 3 is a graph showing plasma levels of mirtazapine over time following a single topical administration of a commercially available compounded transdermal ointment formulation of mirtazapine to each of four healthy cats, as described in Example 2.
Figure 4:
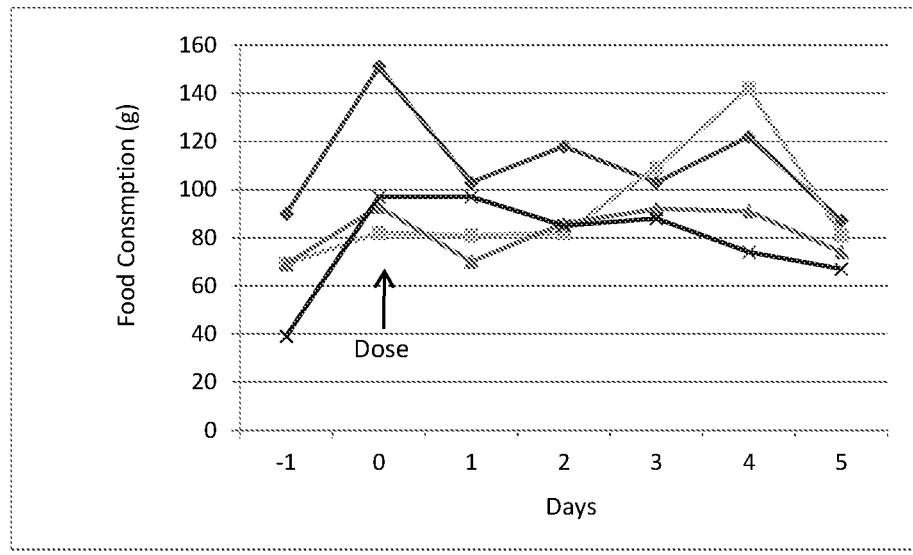
FIG. 4 is a graph showing grams of food consumed over time following a single topical administration of a commercially available compounded transdermal ointment formulation of mirtazapine to each of four healthy cats, as described in Example 2.

The ointment was rubbed onto the surface of the pinna. Venous blood samples were taken at measured intervals to quantify the amount of mirtazapine in the plasma. Food consumption and activity were measured. The cats remained active and demonstrated no adverse effects from the treatment. Plasma concentrations of mirtazapine following topical dosing are summarized in FIG. 3. Peak plasma concentrations of mirtazapine were in the range of 10 to 50 ng/mL (mean 30 ng/mL), the peak concentration occurred at 1 to 12 hours after dosing, the total drug exposure (AUC) was 100 to 500 (mean 285) h*ng/mL, and the half-life was 15 hours. As shown in FIG. 3, plasma concentrations of mirtazapine were variable. Food consumption was either unchanged or increased modestly and was quite variable among the treated cats as shown in FIG. 4. Although the commercial, compounded formulation results in peak concentrations below those associated with toxicity, variability in plasma concentrations and food consumption indicate incomplete transdermal absorption and would make dosing with this formulation inaccurate. Those of ordinary skill in the art will appreciate that the drug exposure for this compounded transdermal formulation as measured by AUC is only about half that obtained using dosing of the oral tablet, as described in Example 1 above.

FIG. 4.

Example 3. Demonstration of Therapeutic Efficacy Using Ointments for Topical (Transdermal) Administration to Stimulate Appetite in Cats Sets of ointment excipients believed to be compatible with the present objectives were prepared and assessed for performance in certain methods provided herein. A variety of formulations were assessed.

In vivo testing of the formulations typically involved applying a measured amount of the ointment test formulation to deliver a dosage of 1.0 mg/kg to the skin of the inner (anterior) surface of the animal's ear flap (pinna). Unless otherwise indicated, four cats were tested for each formulation. The indicated amount of the transdermal ointment was rubbed onto the surface of the pinna by hand. The drug was absorbed through the skin into the systemic circulation. Venous blood samples were taken at measured intervals to quantify the concentration of mirtazapine in the animal's plasma. Appetite and activity were also measured in the treated animals. In all tests for which results are reported here, the cats were active and demonstrated no apparent adverse effects from the treatment.

A. Assessment of Formulation L

The data below show a test of Formulation L in accordance with the above protocol. The results below showed that Formulation L had inadequate performance characteristics. Formulation L has the composition shown in the following table:

TABLE 1

Composition of Formulation L

| Ingredient Name | % (weight) | Function |
| --- | --- | --- |
| Mirtazapine, USP | 4% | API |
| Alcohol, 200 proof, USP | 63.8% | Solvent, Solubilizer, Penetration enhancer |
| Hydroxypropylcellulose, NF | 1.7% | Rheology modifiers |
| Diethylene Glycol Monoethyl Ether (DGME), NF/EP | 19% | Penetration enhancer; Solubilizer |
| PEG-8 Caprylic/Capric Glycerides (Labraso ®), NF | 6.5% | Penetration enhancer; Solubilizer |
| Oleyl Alcohol, NF | 5% | Solubilizer |

Figure 5:
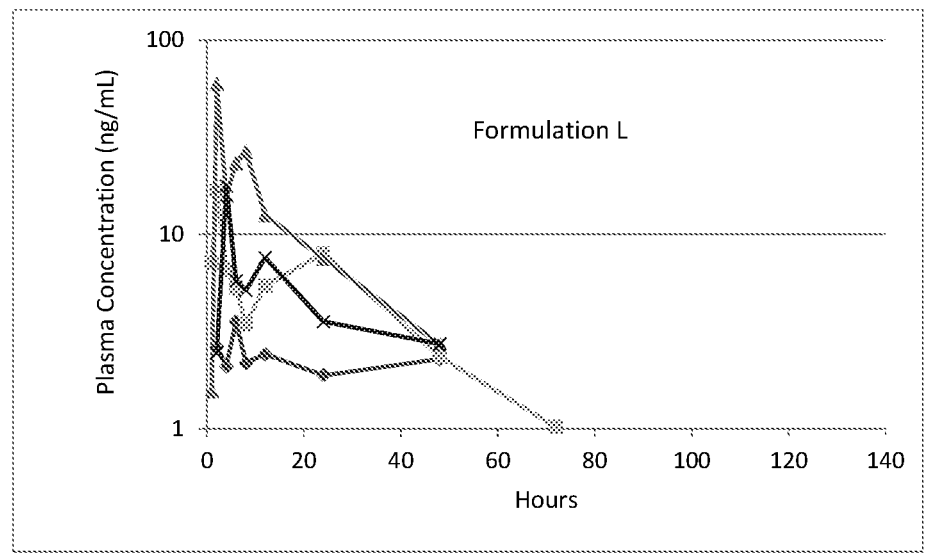
FIG. 5 is a graph showing plasma levels of mirtazapine over time following single dose topical administration of transdermal ointment Formulation L to healthy cats, as described in Example 3A.

The measured plasma concentrations of mirtazapine following topical dosing with Formulation L are shown in FIG. 5. Plasma concentrations were lower than seen with other formulations, such as, for example, with Formulation H (see below), or with the above-described oral dosing (FIG. 1), and are notably more variable than either.

Figure 6:
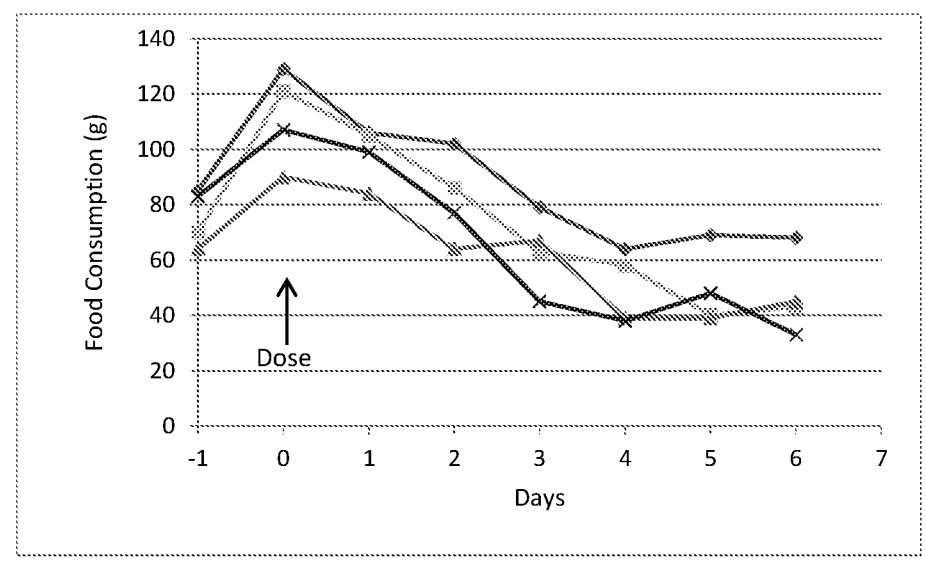
FIG. 6 is a graph showing grams of food consumed over time following single dose topical administration of transdermal ointment Formulation L to healthy cats, as described in Example 3A.

For test Formulation L, peak plasma concentrations of mirtazapine were in the range of 5 to 75 ng/mL (mean 25 ng/mL), the peak concentration occurred at 1 to 12 hours after dosing, the total drug exposure as measured as area under the curve (AUC) is 75 to 750 (mean 280) h*ng/mL, and the half-life could not be calculated because of extreme variability. Appetite was increased as manifested in increased food consumption as shown in FIG. 6. Formulation L results in markedly variable and undesirably lower total drug exposure than other formulations herein, such as Formulation H, demonstrating the superiority of the other formulations over Formulation L. These data clearly show that some transdermal formulations are more effective than others in providing efficient transdermal dosing of mirtazapine.

B. Assessment of Other Transdermal Formulations

Further ointment formulations for transdermal administration of mirtazapine were assessed. Briefly, the other formulations were made generally as follows (the specific steps described are for Formulation T, below). A "PEG Phase" is prepared by the following steps: PEG 400 NF and PEG 3350 NF are placed in a 1500 mL beaker and mixed with a standard blade under nitrogen and heated to 60-70° C., and mixing is continued under nitrogen until the mixture is visually uniform. Then, with continued mixing under nitrogen, the mixture is allowed to cool to 40-50° C., at which point mixing is continued under nitrogen and at that temperature range until the addition of the "Active Phase", which is prepared as follows. In a 600 mL beaker, Diethylene Glycol Monoethyl Ether NF, PEG-8 Caprylic-Capric Glycerides NF, and Oleyl Alcohol NF are added and mixing begun under nitrogen with a standard blade. Mixing is continued under nitrogen until the mixture is visually uniform, at which point mixing under nitrogen is continued while Butylated Hydroxytoluene NF is added and mixed until visually dissolved. With continued mixing under nitrogen, Mirtazapine USP is added and mixed until visually dissolved. The resulting Active Phase is mixed with the PEG phase to form an ointment.

After an ointment made as generally described above was applied to a subject animal's pinna at the desired dosage level, plasma samples were typically taken for 144 hours to quantify mirtazapine concentrations. Appetite and activity were measured in each treated animal. In all tests for which results are reported here, the treated cats were active and demonstrated no apparent adverse effects from the treatment.

A novel ointment form of mirtazapine with improved performance characteristics is referred to herein as "Formulation H," which is prepared generally as described above and contains the ingredients listed in Table 2, below.

TABLE 2

Composition of Formulation H

| Ingredient Name | % (weight) | Function |
| --- | --- | --- |
| Mirtazapine, USP | 4.00% | API |
| Polyethylene Glycol 400, NF/EP | 40.00% | Bulking Agent |
| Polyethylene Glycol 3350, NF/EP | 20.00% | Bulking Agent |
| C12-15 Alcohols Lactate, USP | 1.50% | Spreading Agent |
| Di-ethylene Glycol Monoethyl Ether (DGME), NF/EP | 19.00% | Penetration enhancer; Solubilizer |
| PEG-8 Caprylic/Capric Glycerides (Labraso ®), NF | 6.50% | Penetration enhancer; Solubilizer |
| Oleyl Alcohol, NF | 5.00% | Solubilizer |
| Polydimethylsiloxane fluid (Q7-9120 Silicone Fluid 20 CST), USP | 1.50% | Spreading Agent |
| Aluminum Starch Octenylsuccinate (Dry Flo AF) | 2.50% | Spreading Agent |

Another ointment formulation containing less mirtazapine (2% instead of 4%) is Formulation G, which has the following composition as set forth in Table 3.

TABLE 3

Composition of Formulation G

| Ingredient Name | % (weight) | Function |
| --- | --- | --- |
| Mirtazapine, USP | 2.00% | API |
| Polyethylene Glycol 400, NF/EP | 40.00% | Bulking Agent |
| Polyethylene Glycol 3350, NF/EP | 20.00% | Bulking Agent |
| C12-15 Alcohols Lactate, USP | 3.50% | Spreading Agent |
| Di-ethylene Glycol Monoethyl Ether (DGME), NF/EP | 19.00% | Penetration enhancer; Solubilizer |
| PEG-8 Caprylic/Capric Glycerides (Labraso ®), NF | 6.50% | Penetration enhancer; Solubilizer |
| Oleyl Alcohol, NF | 5.00% | Solubilizer |
| Polydimethylsiloxane fluid (Q7-9120 Silicone Fluid 20 CST), USP | 1.50% | Spreading Agent |
| Aluminum Starch Octenylsuccinate (Dry Flo AF) | 2.50% | Spreading Agent |

Another ointment formulation for transdermal administration of mirtazapine is Formulation T, which contains 2% mirtazapine and the antioxidant butylated hydroxytoluene (BHT) to prevent the oxidation of mirtazapine (formulation G may degrade over time, as monitored in stability studies (conducted at 25° C. and 40° C. over 3 months)). In addition, Formulation T has no C12-15 alcohols lactate. Formulations T and H are contrasted in Table 4, below.

TABLE 4

Composition of Formulations H and T

| | Formula H with 4% Active | | | Formula T with 2% Active | | |
|---|---|---|---|---|---|---|
| Ingredient Name | % Weight | Function | Ingredient Name | % Weight | Function |
| Mirtazapine, USP | 4.00 | API | Mirtazapine, USP | 2.00 | API |
| Polyethylene Glycol 400, NF/EP | 40.00 | Bulking Agent | Polyethylene Glycol 400, NF/EP | 42.01 | Bulking Agent |
| Polyethylene Glycol 3350, NF/EP | 20.00 | Bulking Agent | Polyethylene Glycol 3350, NF/EP | 21.48 | Bulking Agent |
| C12-15 Alcohols Lactate, USP | 1.50 | Spreading Agent | — | — | — |
| Diethylene Glycol Monoethyl Ether (DGME), NF/EP | 19.00 | Penetration enhancer; Solubilizer | Diethylene Glycol Monoethyl Ether (DGME), NF/EP | 19.00 | Penetration enhancer; Solubilizer |
| PEG-8 Caraylic/Capric Glycerides (Labrasol ®), NF | 6.50 | Penetration enhancer; Solubilizer | PEG-8 Capiylic/Capric Glycerides (Labrasol ®), NF | 6.50 | Penetration enhancer; Solubilizer |
| Oleyl Alcohol, USP | 5.00 | Solubilizer | Oleyl Alcohol, USP | 5.00 | Solubilizer |
| Polydimethylsiloxane fluid (Q7-9120 Silicone Fluid 20 CST), USP | 1.50 | Spreading Agent | Polydimethylsiloxane fluid (Q7-9120 Silicone Fluid 20 CST), USP | 1.50 | Spreading Agent |
| Aluminum Starch Octenylsuccinate (Dry Flo AF) or Tapioca Starch Polymethylsilsequioxane Dry Flo TS | 2.50 | Spreading Agent | Aluminum Starch Octenylsuccinate (Dry Flo AF) or Tapioca Starch Polymethylsilsequioxane Dry Flo TS | 2.50 | Spreading Agent |
| — | — | — | Butylated Hydroxytoluene (BHT), USP | 0.01 | Antioxidant |
| | Total = 100% | | | Total = 100% | |

Figure 7:
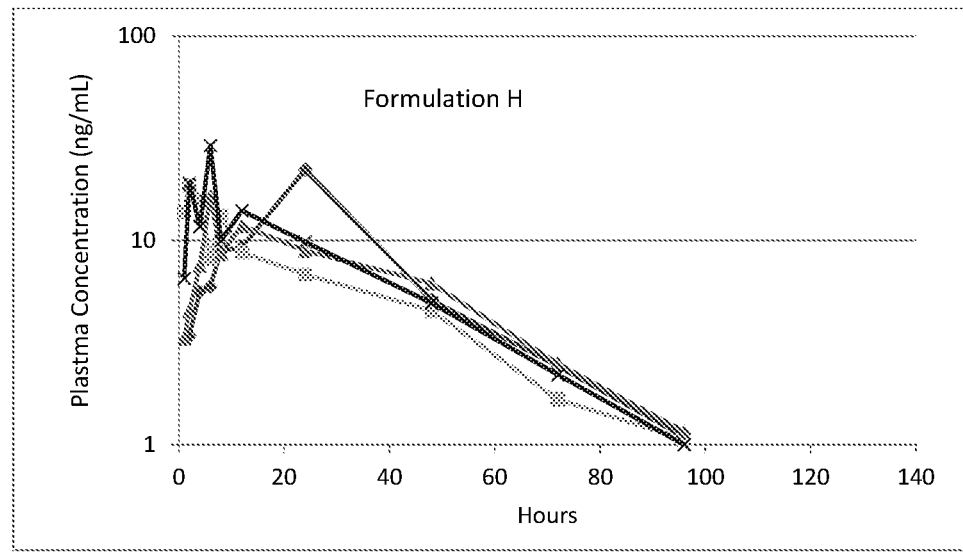
FIG. 7 is a graph showing blood levels of mirtazapine over time following single dose topical administration of transdermal ointment Formulation H to healthy cats, as described in Example 3.
Figure 8:
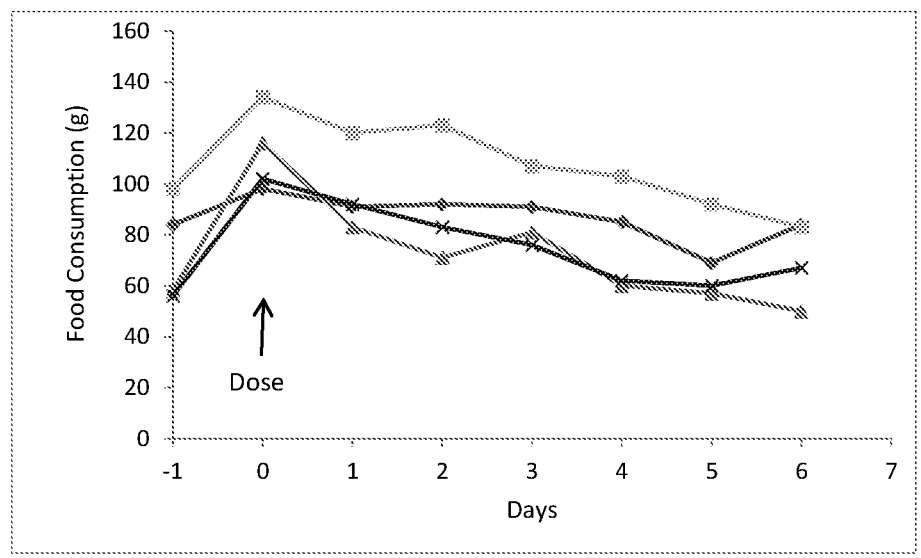
FIG. 8 is a graph showing grams of food consumed over time following single dose topical administration of transdermal ointment Formulation H to healthy cats, as described in Example 3.

Formulation H with Dry Flo AF was tested in cats using a measured amount of the ointment formulation H (Table 2) to deliver a dosage of 1.0 mg/kg through application onto the skin of the inner (anterior) surface of the ear flap (pinna) of four cats, following the protocol set forth above. Plasma concentrations of mirtazapine following topical dosing with Test Formulation H are summarized in FIG. 7. Peak plasma concentrations of mirtazapine using Formulation H were in the range of 10 to 30 ng/mL (mean 22 ng/mL), the peak concentration occurred at 1 to 24 hours after dosing, the total drug exposure as measured as area under the curve (AUC) was 250 to 750 (mean 573) h*ng/mL, and the half-life was approximately 22 hours. Importantly the rate of absorption and the rate of clearance of the drug was slower than both the oral formulation dosing and the commercial compounded topical formulation. Plasma concentrations were more consistent among cats than with the commercially available compounded formulation. Peak concentrations were below those associated with toxicity. These combined attributes make this formulation ideal for once daily dosing and for more consistent absorption from the skin. Appetite was consistently increased as manifested in increased food consumption as shown in FIG. 8.

Formulation H is therefore illustrative of a mirtazapine formulation suitable for topical application. The volume of material applied may be between 0.05 and 0.3 mL per application, for example and without limitation. The concentration of mirtazapine in the formulation can range from about 2 to about 40 mg/mL, for example and without limitation.

Example 4. Demonstration of Therapeutic Efficacy of Mirtazapine Ointment for the Stimulation of Appetite and Weight Gain in Cats For Study A, twenty healthy laboratory cats were randomized to placebo ointment (4 cats), Formulation G ointment (2%), or Formulation H (4%) ointment with Dry-Flo AF and dosed topically on the pinna for 14 days. The dosage was 0.5 or 1.0 mg/kg applied once daily (8 cats per dosing group). For Study B, twenty healthy laboratory cats were randomized to no ointment (4 cats) or Formulation T with Dry-Flo TS ointment (2%) and dosed topically on the pinna for 14 days. The dosage was 0.5 or 2.0 mg/kg applied once daily (8 cats per dosing group). Study B cats wore Elizabethan collars to prevent oral absorption of the ointment.

Figure 9:
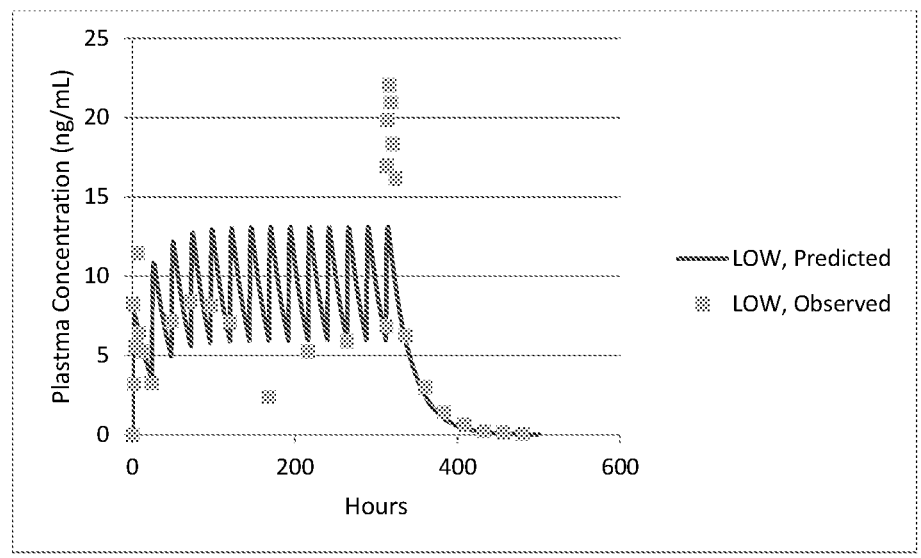
FIG. 9 is a graph showing plasma concentration (ng/mL) versus time (h) profile of mirtazapine following topical application of 2% (0.5 mg/kg/day) ointment to cat pinna, once daily for 13 days, as described in Example 4.
Figure 10:
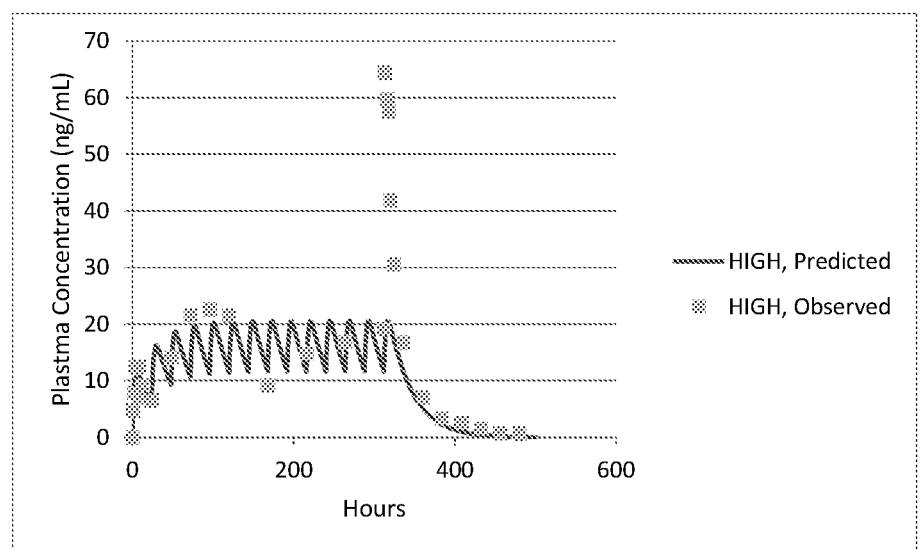
FIG. 10 is a graph showing plasma concentration (ng/mL) versus time (h) profile of mirtazapine following topical application of 4% (1.0 mg/kg/day) ointment to cat pinna, once daily for 13 days, as described in Example 4.

Body weight, daily food consumption, and mirtazapine plasma concentrations were measured, and the results are shown in Table 5. Mirtazapine plasma levels show modest drug accumulation as predicted from pharmacokinetic modelling, and were consistent and predictable among cats dosed with the formulations. (FIGS. 9 and 10). Appetite as measured by daily food consumption was increased during the 14 days of dosing. Increased weight gain and food intake trends were seen in most cats dosed with mirtazapine ointment, but no such changes were seen in the cats dosed with placebo (Table 5). No adverse reactions were observed. Both formulations G and H provided such desirable trends.

Pharmacokinetic results of 14 day dosing are shown in Table 5. In Study A cats did not wear collars that prevent oral absorption of ointment. In Study B cats wore Elizabethan collars to prevent oral absorption. The results show similar PK parameters in the two studies, demonstrating that mirtazapine is being absorbed transdermally when using the ointment formulation described herein.

TABLE 5

PK Parameters following Multiple Doses
of Topical Mirtazapine Ointment[a]

| | Study A Topical | | Study B Topical With Elizabethan Collar | |
|---|---|---|---|---|
| Ointment Conc. | 4% | 2% | 2% | 2% |
| Dosage (mg/kg) | 1.0 | 0.5 | 0.5 | 2.0 |
| $C_{max}$ (ng/mL) | 87 | 26 | 40 | 98 |
| $T_{max}$ (h) | 2 | 5 | 2 | 3 |
| $T_{1/2}$ (h) | 32 | 22 | 21 | 28 |
| $AUC_{0-t}$ (h * ng/mL) | 1446 | 556 | 614 | 1870 |
| $AUC_{0-24}$ (h * ng/mL) | 875 | 358 | 400 | 1000 |
| $AUC_{0-\infty}$ (h * ng/mL) | 1489 | 577 | 647 | 2045 |
| $C_{ave}$ (ng/mL) | 37 | 15 | 16 | 47 |
| ↑ Food Intake | ++ | ++ | − | ++ |
| ↑ Body Weight | ++ | ++ | ++ | ++ |

[a]Values are the mean of eight cats

Figure 11:
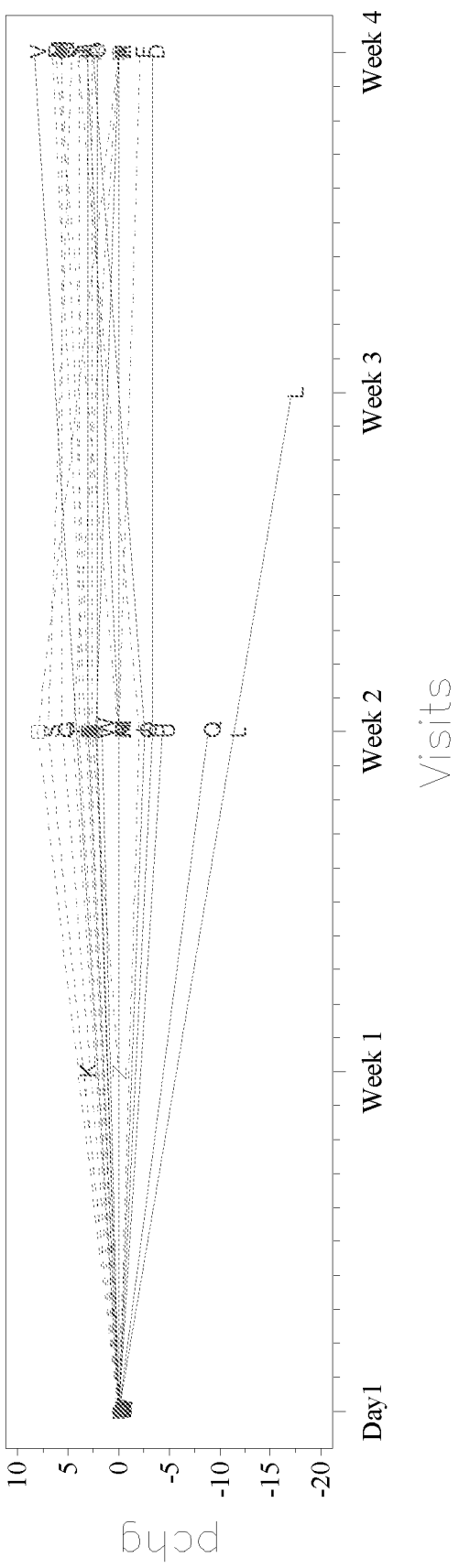
FIG. 11 is a graph showing the percent change in weight over time for cats in the field treated with placebo (solid lines) or mirtazapine formulation (dotted lines), as described in Example 5. Each line represents an individual treated cat.

Example 5. Demonstration of Therapeutic Efficacy of Mirtazapine for the Stimulation of Weight Gain in Cats Client-owned adult cats with sub-optimal body condition score and a history of weight loss were randomized to Formulation T with Dry-Flo TS or a placebo ointment identical to Formulation T with Dry-Flo TS except for the absence of active drug. The dosage was 2.0 mg/kg applied once daily to the pinna. Cats were followed for 4 weeks, with weight measurements taken on day 1, at two weeks and at four weeks. The primary comparison was weight gain. As shown in FIG. 11, cats treated with mirtazapine showed greater percent weight gain compared to cats treated with placebo. At the week 2 timepoint, the percentage change in body weight from baseline in placebo-treated cats was −1.65 (n=11), versus +3.25 (n=13) in the mirtazapine-treated cats (p=0.0042). At the week 4 timepoint, the percentage change in body weight from baseline in placebo-treated cats was +1.44 (n=11), versus +3.39 (n=11) in the mirtazapine-treated cats (p=0.1361). Placebo cats that experienced considerable weight loss at week 2 were dropped from the study, explaining the seemingly improved response in placebo-dosed cats at the week 4 timepoint relative to the earlier timepoints.

Example 6. Container with Mirtazapine Ointment

An exemplary, non-limiting container suitable for use with an ointment provided herein is an aluminum tube with a tapered aluminum tip having an open end. One of ordinary skill in the art will appreciate that a variety of simple configurations are possible (e.g., screw-on cap, flip-top, etc.), the embodiment chosen for a particular application may vary. One consideration is the size of the orifice from which the ointment will be extruded. For a 1.27 mm orifice with a typical ointment provided herein, a dose measured in the form of a ribbon length of 1.25 inch yielded about 0.04 g of material, and even a ribbon length twice that amount (2.5 inches) may not be sufficient for some therapeutic applications. For many therapeutic applications, it may be desirable to use a tube with a larger orifice, e.g., one that will deliver, in a 1.25-1.5 inch long ribbon, about 0.09-0.1 mL on average. A nonlimiting exemplary orifice is 1.6-2 mm diameter, or about 1.8 mm.

While an aluminum tube with a tapered open tip may be somewhat less protective of the drug than other simple container types, stability data from a prototype formulation (Formulation O, which is substantially similar to Formulation T but contains C12-15 Alcohols Lactate; Table 6) shows that the presence of an anti-oxidant such as but not limited to BHT, is sufficient to provide a suitable formulation.

TABLE 6

Formulation O
Formula O with 2% Active

| Ingredient Name | % Weight | Function |
|---|---|---|
| Mirtazapine, USP | 2.00 | API |
| Polyethylene Glycol 400, NF/EP | 40.00 | Bulking Agent |
| Polyethylene Glycol 3350, NF/EP | 20.00 | Bulking Agent |
| C12-15 Alcohols Lactate, USP | 3.49 | Spreading Agent |
| Diethylene Glycol Monoethyl Ether (DGME), NF/EP | 19.00 | Penetration enhancer; Solubilizer |
| PEG-8 Capylic/Capric Glycerides (Labraso ®), NF | 6.50 | Penetration enhancer; Solubilizer |
| Oleyl Alcohol, USP | 5.00 | Solubilizer |
| Polydimethylsiloxane fluid (Q7-9120 Silicone Fluid 20 CST), USP | 1.50 | Spreading Agent |
| Aluminum Starch Octenylsuccinate (Dry Flo AF) or Tapioca Starch Polymethylsilsequioxane Dry Flo TS | 2.50 | Spreading Agent |
| Butylated Hydroxytoluene (BHT), USP | 0.01 | Antioxidant |
| Total = 100% | | |

Formulations with longer shelf life by inclusion of a variety of additives and container choices in accordance with the present disclosure are also provided, including (i) a variety of sealable containers, including, but not limited to, those with screw on lids and sealed single-use applicators, nitrogen blanket pouch containers, and the like, as well as (ii) by formulation changes, increased or more potent anti-oxidants, for example. Ointment manufacturing may also be conducted under nitrogen blanket to prevent degradation of the mirtazapine.

Although the foregoing invention has been descried in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A topical pharmaceutical formulation for the treatment of anorexia and stimulation of appetite and management of weight loss in dogs and cats said formulation comprising 0.2 to 4% mirtazapine, 25-35% penetration enhancer and/or solubilizer, 50-70% bulking agent, and 0-1% antioxidant by weight (w/w).

2. The pharmaceutical formulation of claim 1, wherein said formulation is an ointment.

3. The pharmaceutical formulation of claim 1, which is selected from the group consisting of:
   (i) a formulation comprising 2% mirtazapine, 40% polyethylene glycol 400, 20% polyethylene glycol 3350, 3.5% C12-15 alcohols lactate, 19% di-ethylene glycol monoethyl ether (DGME), 6.5% PEG-8 caprylic/capric glycerides, 5% olelyl alcohol, 1.5% polydimethylsiloxane fluid, and 2.5% aluminum starch octenylsuccinate,
   (ii) a formulation comprising 4% mirtazapine, 40% polyethylene glycol 400, 20% polyethylene glycol 3350, 1.5% C12-15 alcohols lactate, 19% di-ethylene glycol monoethyl ether (DGME), 6.5% PEG-8 caprylic/capric glycerides, 5% olelyl alcohol, 1.5% polydimethylsiloxane fluid, and 2.5% aluminum starch octenylsuccinate,
(iii) a formulation comprising 4% mirtazapine, 40% polyethylene glycol 400, 20% polyethylene glycol 3350, 1.5% C12-15 alcohols lactate, 19% di-ethylene glycol monoethyl ether (DGME), 6.5% PEG-8 caprylic/capric glycerides, 5% olelyl alcohol, 1.5% polydimethylsiloxane fluid, and 2.5% tapioca starch polymethylsilsequioxane,
(iv) a formulation comprising 2% mirtazapine, 40% polyethylene glycol 400, 20% polyethylene glycol 3350, 3.49% C12-15 alcohols lactate, 19% di-ethylene glycol monoethyl ether (DGME), 6.5% PEG-8 caprylic/capric glycerides, 5% olelyl alcohol, 1.5% polydimethylsiloxane fluid, 2.5% aluminum starch octenylsuccinate or tapioca starch polymethylsilsequioxane, and 0.01% butylated hydroxytoluene,
(v) a formulation comprising 2% mirtazapine, 42.01% polyethylene glycol 400, 21.48% polyethylene glycol 3350, 19% di-ethylene glycol monoethyl ether (DGME), 6.5% PEG-8 caprylic/capric glycerides, 5% olelyl alcohol, 1.5% polydimethylsiloxane fluid, 2.5% aluminum starch octenylsuccinate, and 0.01% butylated hydroxytoluene, and
(vi) a formulation comprising 2% mirtazapine, 42.01% polyethylene glycol 400, 21.48% polyethylene glycol 3350, 19% di-ethylene glycol monoethyl ether (DGME), 6.5% PEG-8 caprylic/capric glycerides, 5% olelyl alcohol, 1.5% polydimethylsiloxane fluid, 2.5% tapioca starch polymethylsilsequioxane, and 0.01% butylated hydroxytoluene.

4. A method of applying the formulation of claim comprising topically administering onto the skin of a dog or cat a dose of such formulation sufficient to result in transdermal absorption of a therapeutically effective dose of mirtazapine from the surface of the skin into the systemic circulation.

5. The method of claim 4, wherein the dosage of mirtazapine administered in a single daily dose is in the range of 0.05 to 2 mg/kg of weight of the dog or cat to be treated.

6. The method of claim 5, wherein the ointment placed onto the skin is applied in a volume of 0.05 to 5.0 ml per dose.

7. The method of claim 4, wherein the dose administered is between 0.2 and 5 mg per cat, or between 0.5 and 50 mg per dog.

8. The method of claim 4, wherein the said dog or cat is suffering from anorexia, weight loss, decreased body condition score secondary to renal failure, hepatopathy, the results of surgery, dental disease, neoplasia, old age, or other acute or chronic condition.

9. The method of claim 4, wherein the dose is applied once daily, or every other day, or once weekly, or once every 2 weeks, or monthly.

10. The pharmaceutical formulation of claim 1, wherein the formulation is provided in a container which protects the formulation from moisture, air, and/or light, and wherein the container is a device capable of dispensing a volume of drug product in a range of between 0.05 and 2.0 mL repeatedly and consistently by activation of the device by the user.

11. A method of treating anorexia, stimulating appetite, and/or managing weight loss in a dog or cat, comprising applying an ointment onto the skin of a dog or cat, wherein the ointment comprises 0.2 to 4% mirtazapine 25-35% penetration enhancer and/or solubilizer, 50-70% bulking agent, and 0-1% antioxidant by weight (w/w).

12. The method of claim 11, wherein the dosage of mirtazapine administered in a single daily dose is in the range of 0.05 to 2 mg/kg of weight of the dog or cat to be treated.

13. The method of claim 12, wherein the ointment is applied in a volume of 0.05 to 2.0 ml per dose.

14. The method of claim 11, wherein the dose administered is between 0.2 and 5 mg per cat, or between 0.5 and 50 mg per dog.

15. The method of claim 11, wherein the ointment is applied to the pinna.

16. The method of claim 11, wherein the ointment is selected from the group consisting of:
(i) an ointment comprising 2% mirtazapine, 40% polyethylene glycol 400, 20% polyethylene glycol 3350, 3.5% C12-15 alcohols lactate, 19% di-ethylene glycol monoethyl ether (DGME), 6.5% PEG-8 caprylic/capric glycerides, 5% olelyl alcohol, 1.5% polydimethylsiloxane fluid, and 2.5% aluminum starch octenylsuccinate,
(ii) an ointment comprising 4% mirtazapine, 40% polyethylene glycol 400, 20% polyethylene glycol 3350, 1.5% C12-15 alcohols lactate, 19% di-ethylene glycol monoethyl ether (DGME), 6.5% PEG-8 caprylic/capric glycerides, 5% olelyl alcohol, 1.5% polydimethylsiloxane fluid, and 2.5% aluminum starch octenylsuccinate,
(iii) an ointment comprising 4% mirtazapine, 40% polyethylene glycol 400, 20% polyethylene glycol 3350, 1.5% C12-15 alcohols lactate, 19% di-ethylene glycol monoethyl ether (DGME), 6.5% PEG-8 caprylic/capric glycerides, 5% olelyl alcohol, 1.5% polydimethylsiloxane fluid, and 2.5% tapioca starch polymethylsilsequioxane,
(iv) an ointment comprising 2% mirtazapine, 40% polyethylene glycol 400, 20% polyethylene glycol 3350, 3.49% C12-15 alcohols lactate, 19% di-ethylene glycol monoethyl ether (DGME), 6.5% PEG-8 caprylic/capric glycerides, 5% olelyl alcohol, 1.5% polydimethylsiloxane fluid, 2.5% aluminum starch octenylsuccinate or tapioca starch polymethylsilsequioxane, and 0.01% butylated hydroxytoluene,
(v) an ointment comprising 2% mirtazapine, 42.01% polyethylene glycol 400, 21.48% polyethylene glycol 3350, 19% di-ethylene glycol monoethyl ether (DGME), 6.5% PEG-8 caprylic/capric glycerides, 5% olelyl alcohol, 1.5% polydimethylsiloxane fluid, 2.5% aluminum starch octenylsuccinate, and 0.01% butylated hydroxytoluene, and
(vi) an ointment comprising 2% mirtazapine, 42.01% polyethylene glycol 400, 21.48% polyethylene glycol 3350, 19% di-ethylene glycol monoethyl ether (DGME), 6.5% PEG-8 caprylic/capric glycerides, 5% olelyl alcohol, 1.5% polydimethylsiloxane fluid, 2.5% tapioca starch polymethylsilsequioxane, and 0.01% butylated hydroxytoluene.

17. The pharmaceutical formulation of claim 1, wherein the bulking agent comprises polyethylene glycols.

18. The pharmaceutical formulation of claim 17, wherein the polyethylene glycols include one or more of polyethylene glycol 400, polyethylene glycol 3350, polyethylene glycol 4000, polyethylene glycol 2000, or polyethylene glycol 6000.

19. The pharmaceutical formulation of claim 1, wherein the formulation comprises 0.2-4% mirtazapine, 30-45% polyethylene glycol 400 and 20-25% polyethylene glycol 3350, 15-25% diethylene glycol monoethyl ether (DGME), 5-10% PEG-8 caprylic/capric glycerides, 3-8% oleyl alcohol, 0.5-3% polydimethylsiloxane fluid, and 1-4% Tapioca Starch Polymethylsilsequioxane (Dry Flo TS) by weight (w/w).

20. The pharmaceutical formulation of claim 19, wherein the formulation does not comprise ethanol or hydroxypropylcellulose.

21. The method of claim 4, wherein the formulation comprises 0.2-4% mirtazapine, 30-45% polyethylene glycol 400 and 20-25% polyethylene glycol 3350, 15-25% diethylene glycol monoethyl ether (DGME), 5-10% PEG-8 caprylic/capric glycerides, 3-8% oleyl alcohol, 0.5-3% polydimethylsiloxane fluid, and 1-4% Tapioca Starch Polymethylsilsequioxane (Dry Flo TS) by weight (w/w).

22. The method of claim 4, wherein the ointment is selected from the group consisting of:
   (i) an ointment comprising 2% mirtazapine, 40% polyethylene glycol 400, 20% polyethylene glycol 3350, 3.5% C12-15 alcohols lactate, 19% di-ethylene glycol monoethyl ether (DGME), 6.5% PEG-8 caprylic/capric glycerides, 5% olelyl alcohol, 1.5% polydimethylsiloxane fluid, and 2.5% aluminum starch octenylsuccinate,
   (ii) an ointment comprising 4% mirtazapine, 40% polyethylene glycol 400, 20% polyethylene glycol 3350, 1.5% C12-15 alcohols lactate, 19% di-ethylene glycol monoethyl ether (DGME), 6.5% PEG-8 caprylic/capric glycerides, 5% olelyl alcohol, 1.5% polydimethylsiloxane fluid, and 2.5% aluminum starch octenylsuccinate,
   (iii) an ointment comprising 4% mirtazapine, 40% polyethylene glycol 400, 20% polyethylene glycol 3350, 1.5% C12-15 alcohols lactate, 19% di-ethylene glycol monoethyl ether (DGME), 6.5% PEG-8 caprylic/capric glycerides, 5% olelyl alcohol, 1.5% polydimethylsiloxane fluid, and 2.5% tapioca starch polymethylsilsequioxane,
   (iv) an ointment comprising 2% mirtazapine, 40% polyethylene glycol 400, 20% polyethylene glycol 3350, 3.49% C12-15 alcohols lactate, 19% di-ethylene glycol monoethyl ether (DGME), 6.5% PEG-8 caprylic/capric glycerides, 5% olelyl alcohol, 1.5% polydimethylsiloxane fluid, 2.5% aluminum starch octenylsuccinate or tapioca starch polymethylsilsequioxane, and 0.01% butylated hydroxytoluene,
   (v) an ointment comprising 2% mirtazapine, 42.01% polyethylene glycol 400, 21.48% polyethylene glycol 3350, 19% di-ethylene glycol monoethyl ether (DGME), 6.5% PEG-8 caprylic/capric glycerides, 5% olelyl alcohol, 1.5% polydimethylsiloxane fluid, 2.5% aluminum starch octenylsuccinate, and 0.01% butylated hydroxytoluene, and
   (vi) an ointment comprising 2% mirtazapine, 42.01% polyethylene glycol 400, 21.48% polyethylene glycol 3350, 19% di-ethylene glycol monoethyl ether (DGME), 6.5% PEG-8 caprylic/capric glycerides, 5% olelyl alcohol, 1.5% polydimethylsiloxane fluid, 2.5% tapioca starch polymethylsilsequioxane, and 0.01% butylated hydroxytoluene.

23. The method of claim 11, wherein the formulation comprises 0.2-4% mirtazapine, 30-45% polyethylene glycol 400 and 20-25% polyethylene glycol 3350, 15-25% diethylene glycol monoethyl ether (DGME), 5-10% PEG-8 caprylic/capric glycerides, 3-8% oleyl alcohol, 0.5-3% polydimethylsiloxane fluid, and 1-4% Tapioca Starch Polymethylsilsequioxane (Dry Flo TS) by weight (w/w).

24. The pharmaceutical formulation of claim 1, wherein the formulation comprises 2% or 4% mirtazapine by weight (w/w).

25. The method of claim 4, wherein the formulation comprises 2% or 4% mirtazapine by weight (w/w).

26. The method of claim 11, wherein the formulation comprises 2% or 4% mirtazapine by weight (w/w).

27. The pharmaceutical formulation of claim 1, comprising a spreading agent.

28. The pharmaceutical formulation of claim 27, wherein the formulation comprises 4-7.5% spreading agent.

29. The method of claim 4, wherein the formulation comprises a spreading agent.

30. The method of claim 29, wherein the formulation comprises 4-7.5% spreading agent.

31. The method of claim 11, wherein the formulation comprises a spreading agent.

32. The method of claim 31, wherein the formulation comprises 4-7.5% spreading agent.

* * * * *

UNITED STATES PATENT AND TRADEMARK OFFICE
CERTIFICATE OF CORRECTION

PATENT NO. : 10,603,272 B2
APPLICATION NO. : 15/551847
DATED : March 31, 2020
INVENTOR(S) : William Buhles et al.

It is certified that error appears in the above-identified patent and that said Letters Patent is hereby corrected as shown below:

In Claim 4, Column 19, Line 34, "claim comprising" should read --claim 1, comprising--.

Signed and Sealed this
Fourth Day of August, 2020

Andrei Iancu
*Director of the United States Patent and Trademark Office*